(12) United States Patent
Liu et al.

(10) Patent No.: US 8,414,930 B2
(45) Date of Patent: Apr. 9, 2013

(54) SURGICAL CALCIUM PHOSPHATE CITRATE-CONTAINING CEMENT AND METHOD OF MANUFACTURING THE SAME

(75) Inventors: Sung-Tsuen Liu, Miaoli County (TW); Sung-Ching Chen, New Taipei (TW); Hui-Chun Lai, New Taipei (TW); Kehsin Chien, New Taipei (TW)

(73) Assignee: Maxigen Biotech Inc., New Taipei (TW)

( * ) Notice: Subject to any disclaimer, the term of this patent is extended or adjusted under 35 U.S.C. 154(b) by 51 days.

(21) Appl. No.: 13/004,560

(22) Filed: Jan. 11, 2011

(65) Prior Publication Data
US 2012/0178684 A1 Jul. 12, 2012

(51) Int. Cl.
*C04B 35/00* (2006.01)
(52) U.S. Cl.
USPC .................................. 424/602; 106/35; 501/1
(58) Field of Classification Search .................. None
See application file for complete search history.

(56) References Cited

U.S. PATENT DOCUMENTS

| | | | |
|---|---|---|---|
| 4,518,430 A | 5/1985 | Brown et al. | |
| 4,612,053 A | 9/1986 | Brown et al. | |
| 5,149,368 A | 9/1992 | Liu et al. | |
| 5,208,372 A | * 5/1993 | Vidal et al. | 562/584 |
| 5,262,166 A | 11/1993 | Liu et al. | |

* cited by examiner

*Primary Examiner* — Elizabeth C Kemmerer
(74) *Attorney, Agent, or Firm* — WPAT, P.C.; Anthony King

(57) ABSTRACT

The present invention discloses a surgical cement and a manufacturing method thereof. The surgical cement comprises a cementing component selected form the group of a basic calcium phosphate consisting of tetracalcium phosphate, alpha-tricalcium phosphate, decomposed hydroxyapatite, or a combination thereof; a setting reagent selected form the group of an acidic calcium citrate consisting of monocalcium citrate, dicalcium citrate, or a combination thereof; and water; wherein a weight ratio of the cementing component and the setting reagent ranges from about 1:1 to about 8:1. The surgical cement is bioresorbable and bioactive and is useful in orthopedic, maxillofacial and dental applications. In addition, the surgical cement of this invention has a good flow character and a relatively short setting time.

21 Claims, 2 Drawing Sheets

SURGICAL CALCIUM PHOSPHATE CITRATE-CONTAINING CEMENT AND METHOD OF MANUFACTURING THE SAME

BACKGROUND OF THE INVENTION

1. Field of the Invention

The present invention relates to a surgical cement, also known as bone cement or bioresorbable implantation, and more particularly to a surgical calcium phosphate citrate-containing cement that is bioresorbable and bioactive for orthopedic, dental, and maxillofacial applications and a manufacturing method thereof.

2. Description of Related Art

The major inorganic constitution of hard tissues is biological apatite. Hydroxyapatite (HA) is a calcium phosphate compound which has same crystal structure as the biological apatite. In principle, HA should be an ideal candidate as a hard tissue replacement material. However, the precipitated HA has a very fine particle size. Because of manipulation requirement, this hinders the applications of precipitated HA in the medical area.

Many types of calcium phosphate ceramics have been prepared by a high temperature sintering technique, and have been approved as useful and biocompatible materials for bone substitutes. These include tetracalcium phosphate (TTCP), HA, alpha-tricalcium phosphate ($\alpha$-TCP) and beta-tricalcium phosphate ($\beta$-TCP), calcium pyrophosphate, and biphasic calcium phosphate (BPC) ceramics. Most of the calcium phosphate ceramics for medical application are prepared either as a granular form or block form. The granular form has a mobility problem while the block form is very brittle and is difficult to shape. In order to solve the above problem, many attempts have been made to prepare bioresorbable grouts or cement materials as binder for the granule form of the calcium phosphate ceramics. Among these are Plaster of Paris, collagen, polymers and several types of calcium phosphate cements.

Chow and his coworkers (U.S. Pat. Nos. 4,518,430 and 4,612,053) started the development of calcium phosphate cement about twenty-five years ago. The first calcium phosphate cement is based on the interaction of TTCP and dicalcium phosphate (DCP) to form hardened cement with a final product which is HA. After that, many modifications on the HA cement have been made by adding setting time regulators or other reagents to improve the flow character. However, the HA cement is resorbed very slowly and does not set well in a wet environment. Beside, its flow character is poor. Another type of calcium phosphate cement developed is dicalcium phosphate dihydrate (DCPD). The basic constitution of this type of cement is a basic calcium phosphate compound having a Ca/P mole ratio greater than 1 with monocalcium phosphate monohydrate, monocalcium phosphate anhydrous or phosphoric acid. The common basic calcium phosphate compounds used are tricalcium phosphate (TCP) and HA. Sometimes, calcium oxide or calcium carbonate can also be used. Disadvantages of this type of cement are very acidic at the time of setting, poor flow, and weak mechanical strength and difficult to get a consistent result. Therefore, this type of cement normally keeps the basic components in excess. After setting, there are some unreacted components together with the reaction product, DCPD. This type of cement also does not set well in a liquid environment.

The majorities of calcium phosphate (CP) cements are either HA cement or DCP cement. Both types of cements use calcium phosphate compounds only, one with a higher Ca/P mole ratio while the other with a lower Ca/P mole ratio. The most common compounds with high Ca/P mole ratios are TTCP, HA and TCP. In the past, some attempts have been made by using these calcium phosphate compounds having high Ca/P ratios as cementing components, and using other soluble non-calcium phosphate containing acidic compounds as setting reagents. These acidic compounds include phosphoric acid, bi-functional organic acids, citric acid and polycyclic acid. These cements are normally very acidic in nature and take a very long time to reach a neutral pH. After implantation, these cements would cause irritation and inflammatory reactions. Beside, these cements are difficult to control bioresorpion and do not have a good manipulation character. Other bone cement utilizes soluble alkaline silicate as a setting solution. The reaction product is calcium silicate.

A resorbable bioactive calcium phosphate cement was proposed by S. T. Liu et al. in U.S. Pat. No. 5,149,368, comprising a cementing powder of TTCP, a setting reagent consisting of an acidic citrate salt, and sufficient water to form a cementitious paste. S. T. Liu et al. further proposed a resorbable bioactive phosphate containing cement in U.S. Pat. No. 5,262,166, in which this surgical cement comprises a cementing powder consisting of calcium sodium phosphate or calcium potassium phosphate ceramics, a setting reagent consisting of citric acid or acidic citrate salts, and water. In both the patents, the acidic citrate salt is selected from the group consisting of soluble $NaH_2$ citrate, $Na_2H$ citrate, $KH_2$ citrate, $K_2H$ citrate, $NH_4H_2$ citrate, and $(NH_4)_2H$ citrate.

However, using soluble citric acid or soluble acidic citrate, such as $NaH_2$ citrate, $Na_2H$ citrate, $KH_2$ citrate, $K_2H$ citrate, $NH_4H_2$ citrate, and $(NH_4)_2H$ citrate, as the setting reagent, the setting time is very sensitive to the used amount of the acidic setting reagent. The solubility of calcium phosphate compounds depends strongly on the pH of the solution. At pH around 7, the solubility of calcium phosphate compounds follow the order TTCP>$\alpha$-TCP>$\beta$-TCP>HA. The decomposed HA which contains both TTCP and $\alpha$-TCP should also have higher solubility than $\beta$-TCP and HA. By reacting the calcium phosphate compound, having a Ca/P mole ratio equal to 1.5 or higher, with citric aid, it will produce calcium ions, phosphate ions and citrate ions to form other calcium phosphate compounds and corresponding calcium citrate, such as monocalcium citrate ($Ca(H_2\ Citrate)_2$), dicalcium citrate (CaH Citrate), tricalcium citrate ($Ca_3\ Citrate_2$) or a calcium phosphate citrate complex depending on the pH of the solution. Whether the calcium phosphate compound can form setting cement with citric aid or not strongly depends on the nature of calcium phosphate compounds. For example, TTCP, $\alpha$-TCP, or decomposed HA which has high solubility and a high dissolution rate is able to form cement with citric acid in a relatively short time, within 15 minutes. Nevertheless, it is essential precondition that a ratio of the calcium phosphate to citric acid should stays relatively high, normally higher than 3. The more the amount of citric acid, the cement has longer setting time and is more acidic. If the ratio is near 3 or lower, the mixture paste does not set within one hour. Thus, the suitable amount of citric acid for setting stays in a rather narrow range. For the $\beta$-TCP or HA, because of their low dissolution rate, it can form paste with citric acid, but will not set and become hardened at all.

Ideally, a useful cementing material for hard tissue application should have good biocompatibility, a suitable bioresorption rate, and a good setting character with a reasonable setting time. Most of the above cements have certain disadvantages.

SUMMARY OF THE INVENTION

Accordingly, an objective of the present invention is to provide a surgical cement and a manufacturing method thereof for providing a good flow character, controllable resorption rate, nice setting behavior in an aqueous environment and suitable setting time.

According to the objective of the present invention, a surgical cement for orthopedic, dental, and maxillofacial applications comprises a cementing component selected from the group of a basic calcium phosphate consisting of tetracalcium phosphate (TTCP), alpha-tricalcium phosphate (α-TCP), decomposed hydroxyapatite (HA), and a combination thereof; a setting reagent selected from the group of an acidic calcium citrate consisting of sparingly soluble monocalcium citrate ($Ca(H_2 Citrate)_2$), dicalcium citrate (CaH Citrate), and a combination thereof; and water. Wherein, a weight ratio of the cementing component and the setting reagent ranges from about 1:1 to about 8:1.

Preferably, the decomposed HA is partially or fully decomposed HA comprising tetracalcium phosphate (TTCP) and α-TCP.

Preferably, the surgical cement of the present invention has the setting time of about 3 minutes to about 20 minutes. More preferably, the surgical cement of the present invention has the setting time of about 5 minutes to about 15 minutes.

In addition, a method of manufacturing surgical cement for orthopedic, dental, and maxillofacial applications is also provided, comprising the steps. A basic calcium phosphate cementing component is admixed with an acidic calcium citrate setting reagent by a weight ratio ranging from about 1:1 to about 8:1. A desired amount of water is added to obtain a mixture. The mixture is then kneaded to obtain a cementitious paste. Wherein, the basic calcium phosphate cementing component is selected from the group consisting of TTCP, α-TCP, decomposed HA, and a combination thereof; and the acidic calcium citrate setting reagent is selected from the group consisting of $Ca(H_2Citrate)_2$, CaH Citrate, and a combination thereof.

Preferably, the decomposed HA is decomposed partially or fully to form α-TCP and TTCP before the admixing step.

In brief, the surgical cement and the method of manufacturing the same in accordance with the present invention provide one or more of the following advantages:

(1) Unlike the other cements using soluble citric acid or soluble acidic citrate as setting reagent, the present cement using sparingly soluble acidic calcium citrate as setting reagent. The setting time is less sensitive to the amount of acidic reagent used, and thereby the acidic setting reagent used in the present invention can be varied in wide ranges. Furthermore, the more the acidic setting reagent is used, the more highly resorbable the product. This in turn will provide flexibility in controlling the bioresorption rate.

(2) Because of the high cohesive nature, the surgical cement in accordance with the present invention is able to accommodate a large amount of biocompatible fillers such as calcium sulfate, dicalcium phosphate (DCP), HA, gelatin, collagen or mineralized collagen. This further enhances the degree of easiness in better controlling the bioresorption rate of the present cement.

(3) The surgical cement provided by the present invention has good biocompatibility by using the cementing components which are well accepted by the body. Additionally, the present cement has excellent flexibility in controlling the biorseorption rate as well as easy flow and good manipulation characteristics. Consequently, the present cement has greater usefulness as implants for hard tissue replacement materials over the prior art. For example, the present cement can be used for a bone graft, bone fracture fixation, bone defect filler, maxillofacial surgery, spinal fusion, bone cement, dental cement, and drug delivery system for antibiotic drugs and bone growth factors and bone morphogenetic proteins. The present cement can also be used as binder for the granule or powder for other biocompatibility material.

Other aspects of the present invention will be illustrated partially in the subsequent detailed descriptions, conveniently considered partially through the teachings thereof, or comprehended by means of the disclosed embodiments of the present invention. Various aspects of the present invention can be understood and accomplished by using the components and combinations specifically pointed out in the following claims. It is noted that the aforementioned summary and the following detailed descriptions of the present invention are exemplary and illustrative, rather than being used to limit the scope of the present invention thereto.

BRIEF DESCRIPTION OF THE DRAWINGS

The exemplary embodiments of the present invention will be understood more fully from the detailed description given below and from the accompanying drawings of various embodiments of the invention.

DETAILED DESCRIPTION OF THE PREFERRED EMBODIMENTS

Figure 1:
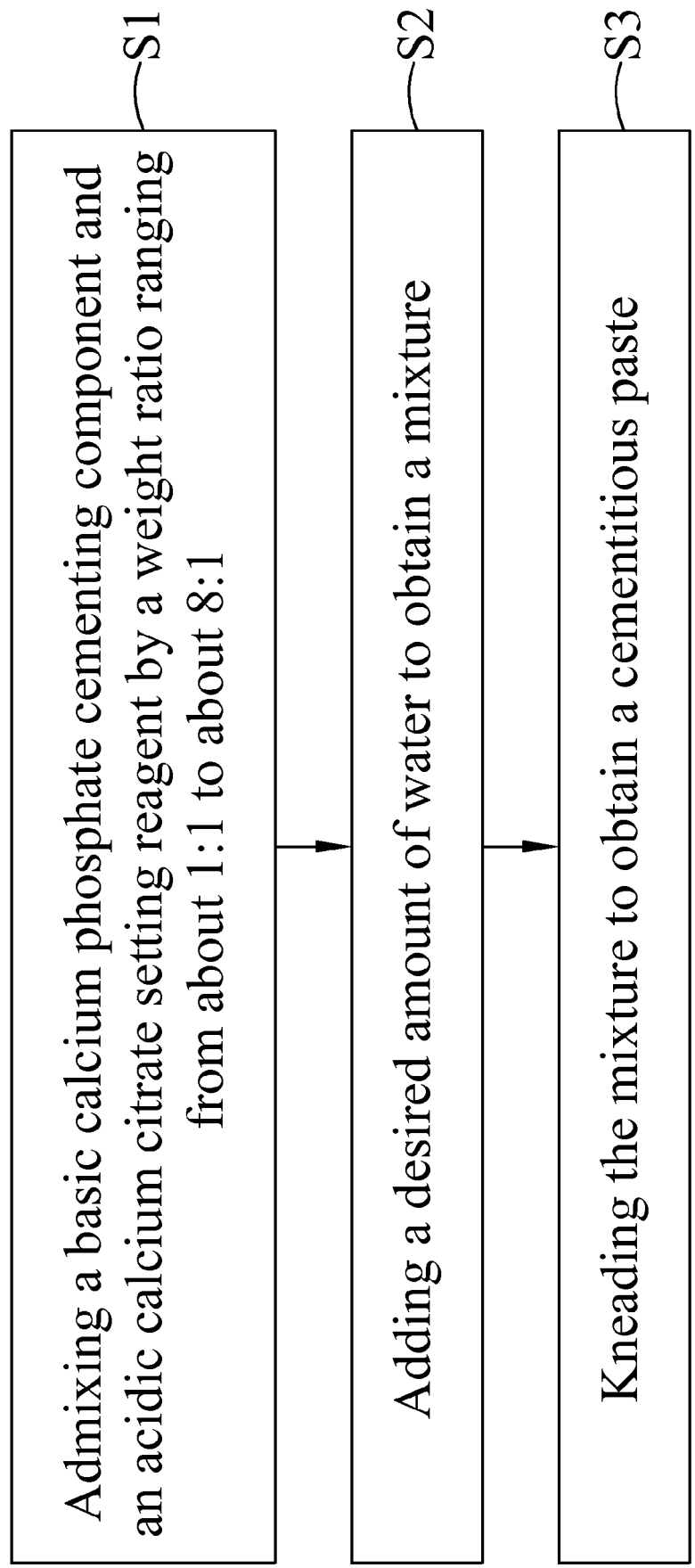
FIG. 1 illustrates a flow chart of a method of manufacturing surgical cement in accordance with an embodiment of the present invention.

Referring to FIG. 1, which is a flow chart of a method of manufacturing surgical cement in accordance with an embodiment of the present invention. The method comprises the following steps. In step S1, a basic calcium phosphate cementing component is admixed with an acidic calcium citrate setting reagent by a weight ratio ranging from about 1:1 to about 8:1. In step S2, a desired amount of water is added to obtain a mixture, and in step S3, the mixture is then kneaded to obtain a cementitious paste. Wherein, the basic calcium phosphate cementing component is selected from the group consisting of tetracalcium phosphate (TTCP), alpha-tricalcium phosphate (α-TCP), decomposed hydroxyapatite (HA), and a combination thereof; and the acidic calcium citrate setting reagent is selected from the group consisting of monocalcium citrate ($Ca(H_2Citrate)_2$), dicalcium citrate (CaH Citrate), and a combination thereof.

Figure 2:
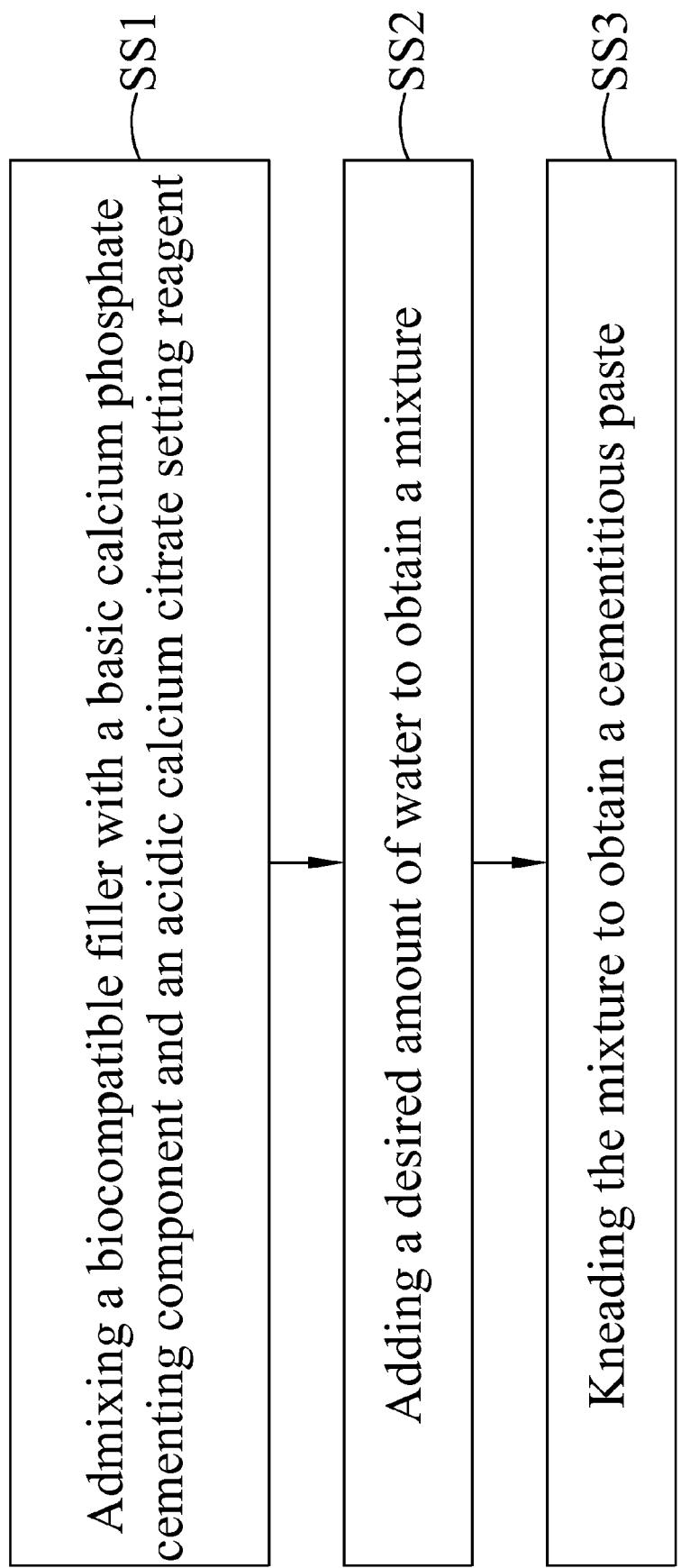
FIG. 2 illustrates a flow chart of a method of manufacturing surgical cement in accordance with another embodiment of the present invention.

Referring to FIG. 2, which is a flow chart of a method of manufacturing surgical cement in accordance with another embodiment of the present invention. The method comprises the steps as follows. In step SS1, a biocompatible filler is admixed with a basic calcium phosphate cementing component and an acidic calcium citrate setting reagent. In step SS2, a desired amount of water is added to obtain a mixture, and in step SS3, the mixture is kneaded to obtain a cementitious paste. Wherein, the weight ratio of the basic calcium phosphate cementing component to the acidic calcium citrate setting reagent is in a range of from about 1:1 to about 8:1. The basic calcium phosphate cementing component is selected from the group consisting of tetracalcium phosphate (TTCP), alpha-tricalcium phosphate (α-TCP), decomposed hydroxyapatite (HA), and a combination thereof; and the acidic calcium citrate setting reagent is selected from the group consisting of monocalcium citrate ($Ca(H_2Citrate)_2$), dicalcium citrate (CaH Citrate), and a combination thereof.

The above biocompatible filler may be selected from a group consisting of α-TCP, beta-tricalcium phosphate (β-TCP), TTCP, octacalcium phosphate, calcium phosphate apatite, dicalcium phosphate dehydrate (DCPD), dicalcium phosphate anhydrous, calcium carbonate, coral, calcium sulfate dihydrate, calcium sulfate hemihydrate, calcium sulfate anhydrous, calcium oxide, calcium hydroxide, calcium fluoride, magnesium oxide, magnesium hydroxide, calcium citrate, gelatin, collagen, chitosan, chitin, mineralized collagen, and a combination thereof. Preferably, the biocompatible filler has a particle size ranging from 5 μm to 2 mm. The biocompatible filler can be up to about 80% by weight based on a total weight of the surgical cement.

Wherein, the obtained cementitious paste may have a setting time of about 3 to 20 minutes, preferably about 5 to 15 minutes. The cementitious paste can be molded into any desired shape and stay in water without disintegration before setting.

In also another embodiment, the decomposed HA may be decomposed partially or fully to form α-TCP and tetracalcium phosphate (TTCP) before the step S1 or the step SS1.

In still another embodiment, the method further comprises a step of adding a soluble pH adjusting reagent; or a step of adding an antibiotic, a drug, a bone growth factor, or a bone morphogenetic protein. Wherein, the soluble pH adjusting reagent may be selected from the group consisting of phosphoric acid, citric acid, NaOH, KOH, $NH_4OH$, $Na_3$ Citrate, $K_3$ Citrate, $(NH_4)_3$ Citrate, $Na_3PO_4$, $K_3PO_4$, and a combination thereof. The antibiotic may be up to about 20% by weight antibiotics based on the total weight of the surgical cement.

In other embodiments, the surgical cements are provided according to the above-mentioned methods and conditions.

The surgical cement of the present invention is formed from calcium phosphates and sparingly soluble non-phosphate containing acidic compounds, which forms a moldable paste having high biocompatibility when combined with an aqueous solution. The paste is easy to manipulate and has a good flow character and workable setting time. The cementing paste has excellent resistance to disintegration in an aqueous solution shortly before setting. The resulting cements are useful in orthopedic and maxillofacial surgeries and in dental applications.

Therefore, the present invention provides a new surgical cement with a good flow character, nice setting behavior in an aqueous environment, suitable setting time from about 5 to 15 minutes and flexible composition for controlling resorption time. The present cements include basic cementing components and acidic setting reagents. The basic cementing components selected include relative high solubility calcium compounds, such as TTCP, α-TCP and decomposed HA. The acidic setting reagents used are sparingly soluble acidic calcium citrates, such as monocalcium citrate or a combination of monocalcium citrate with dicalcium citrate. A setting solution may be pure water, distilled water or saline water. When the cementing component and setting reagent mixed with water, they will form a cementitious paste. At this stage, the paste can then be pasted into the bone defect or injected into the bone defect. The paste will set in situ and becomes hardened in a range of from about 3 to 20 minutes, preferably about 5 to 15 minutes. As the paste become more viscous, it can be easily injected and stay very well in water without disintegration shortly before setting. The paste has strong cohesive strength even without using the binder. Alternatively, the paste can be molded into any desired shape and dries for future use.

Among the calcium phosphate salts, the monocalcium phosphate is acidic while the aqueous suspensions of dicalcium phosphate (DCP), TCP or HA show near neutral pH because of low solubility. The only calcium phosphate ceramics which shows strong alkaline character is tetracalcium phosphate (TTCP). The present cements apply sparingly soluble acidic calcium citrates instead of soluble citric acids or soluble citrate salts, such as $NaH_2$ citrate, $Na_2H$ citrate, $KH_2$ citrate, $K_2H$ citrate, $NH_4H_2$ citrate, and $(NH_4)_2H$ citrate, as the setting reagent. The acidic calcium citrate may be $Ca(H_2Citrate)_2$, or the combination of $Ca(H_2Citrate)_2$ and CaH Citrate. The pH of the citric acid solution is near 2. The pH of the $Ca(H_2Citrate)_2$ suspensions is about 3 or slightly higher. Therefore, the surface pH of the present cement using acidic calcium citrate is higher than those using citric acid. Beside, the setting time of the present cement using acidic calcium citrate is less sensitive to the amount of acidic citrate used. A relatively large amount of acidic calcium citrate can be used to form hardened cement with high soluble calcium phosphates listed above. This in turn will provide the advantage of controlling the resorption rate since higher amount of acidic calcium citrate used will produce more highly resorbed reaction product.

The bioresorption rate of the surgical cements is a major concern for the application of the cement as the hard tissue replacement material. For the young children, the resorbable bone substitute is preferable. The initial setting cement contains the reaction products such as dicalcium phosphate dihydrate or other calcium phosphates and different types of calcium citrates together with unreacted original calcium phosphates. The reaction products are normally resorbed faster than the unreacted original calcium phosphates. Therefore, changing the weigh ratio of calcium phosphate to acidic citrate would be able to change the bioresorption rate. In the present invention, the weight ratio value of the basic calcium phosphate to the acidic calcium citrate stays as low as 1. The ratio value can raises to 3 or 4, even 8.

Because of the high cohesive strength of the surgical cement according to the present invention, it can accommodate a large amount of biocompatible materials in the form as fine powder or granule as filler. The particle size of the filler ranges from few micronmeters to about 1-2 mm. Besides having good biocompatibility, the filler should not show a significant effect on the integrity and setting behavior of the cement. These useful fillers include β-TCP, DCPD, calcium phosphate apatite, calcium carbonate, coral, calcium sulfate dihydrate, calcium sulfate hemihydrate, calcium sulfate anhydrous, calcium fluoride, calcium oxide, magnesium oxide, calcium citrate, gelatin, collage and mineralized collagen. The suitable fillers can be ranged from very slow resorbable materials, such as calcium phosphate apatite material, to very fast resorbable material, such as calcium sulfate, calcium carbonate, calcium oxide and gelatin. This further enhances the flexibility of the current cement in controlling the bioresorption rate.

In surgical cements of the present invention, the basic cementing component, acidic setting reagent and the filler are premixed to form a homogeneous mixed powder. The premixed powders are then pasted with sterilized water or saline water to form a workable paste in the surgical site. These workable pastes are then pasted into the bone defect. Other way of delivery is injected by syringe to the bone defect. After putting into the bone defect, it would set and become hardened in a few minutes. Alternatively, the paste can be pre-set to any shape before use. For example, in the use as a drug delivery system, the required amount of the drug is mixed with the cementing component, setting reagent and filler to form a pre-mixed powder first. After set time, the hardened cement may be broken into a suitable size of granule form. This drug containing cement is then dried and stored before use.

Beside the filler, the present cement may also be added with a pH adjusting agent, drug, antibiotic, growth factor or bone morphogenetic protein. The cement of present invention may be used as bioresorbable cement for 1) bone grafts, bone defect filler or replacement of bone that has been removed surgically or due to trauma; 2) material for ridge augmentations; 3) jaw repairs; 4) cranial and maxillofacial surgeries; 5) luting cement in dentistry and orthopedic surgeries; 6) spinal fusion; 7) endodontic filling materials; 8) root cement; 9) replacing or promoting regeneration of bone mineral lost due to periodontal disease; and 10) drug release systems. Antibiotics are the preferred drugs to be released by the cement of this invention.

EXAMPLES

Materials used: The acidic calcium citrate salts such as $Ca(H_2 Citrate)_2$ and CaH Citrate are prepared by reacting stochiometic amount of citric acid, calcium carbonate or calcium hydroxide with the minimum amount of water to induce the precipitation of the required salt. After precipitation, the whole precipitated material was air dried. The dried precipitated cake was ground to 150 mesh. Pure HA ceramics was decomposed by high temperature treatment to form α-TCP and TTCP. α-TCP was prepared from the precipitation method. The precipitated calcium phosphate cake was the sintered at high temperature and quenched to form α-TCP ceramics. The sintered cake was ground to 150 mesh for use.

Example 1

2 g decomposed HA was mixed with 1.2 g $Ca(H_2 Citrate)_2$, and 0.35 g CaH Citrate. The mixed powder was then further mixed with 1.2 ml of pure water to form a paste. The paste flowed well within 2-6 minutes. A small amount of the paste was added into water at 5 minutes after preparation. This small piece of paste stayed very well in water and did not deform or disintegrate, and set well in water. The paste set at 8 minutes and became hard. After that, the hardened cement was aged in water. The setting cement was still very hard and did not show any sign of disintegration after aging in water for several months.

Examples 2-6

Experiments 2 to 6 were designed to study the effect of acidic monocalcium citrate on the setting time of the cement. In each of these experiments, 1 g of decomposed HA was used. The amounts of $Ca(H_2 Citrate)_2$ and water used were varied. The results are shown in Table 1.

TABLE 1

Showing the setting time

| Experi. No. | Amount of $Ca(H_2Citrate)_2$ (g) | Amount of $H_2O$ (g) | Setting time (min) |
|---|---|---|---|
| 2 | 0.4 | 0.5 | 7-8 |
| 3 | 0.5 | 0.5 | 7-8 |
| 4 | 0.6 | 0.5 | 7-8 |
| 5 | 0.8 | 0.6 | 8-9 |
| 6 | 1.0 | 0.7 | 11 |

The setting time varies with the amount of acidic monocalcium citrate used. When the amount of $Ca(H_2 Citrate)_2$ used varies from 0.4 g to 0.6 g, the setting time stays the same. When the amount changes from 0.6 g to 1.0 g, the changes of setting time are rather mild.

Example 7

2 g of α-TCP as mixed with 0.5 g $Ca(H_2 Citrate)_2$ first. The mixed powder was then further mixed with 0.8 ml of water. The paste flow well at beginning few minutes. The paste set at around 6 minutes. The setting cement stays very strong in water for several months.

Examples 8-10

Experiments 8 to 10 were designed to study the effect of acidic monocalcium citrate on the setting time of the cement. In each of these experiments, 1 g of TTCP was used. The amounts of $Ca(H_2 Citrate)_2$ and water used were varied. The results are shown in Table 2.

TABLE 2

Showing the setting time

| Experi. No. | Amount of $Ca(H_2Citrate)_2$ (g) | Amount of $H_2O$ (g) | Setting time (min) |
|---|---|---|---|
| 8 | 0.5 | 0.5 | 6-7 |
| 9 | 0.6 | 0.6 | 8-9 |
| 10 | 0.8 | 0.8 | 10-11 |

Examples 11-14

Experiments 11 to 14 were designed with non-reactive filler such as calcium sulfate, DCPD and mineralized collagen. In each experiment using 1 g of decomposed HA.

| Experi. No. | Amount of $Ca(H_2 Citrate)_2$ (g) | Amount of $H_2O$ (ml) | Filler | Setting time (min) | Remark |
|---|---|---|---|---|---|
| 11 | 0.6 | 0.8 | 1 g sintered HA (10-20 mesh) | 6 | Aging in water for 2 weeks still strong |
| 12 | 0.6 | 1.0 | 1 g DCPD | 6 | Staying in water for two weeks still strong |
| 13 | 0.7 | 0.9 | 1 g calcium sulfate anhydrous | 9-10 | The paste flow well and can be injected by syringe |
| 14 | 0.6 | 0.5 | 0.1 g mineralized collagen | 10 | The setting cement stays very well in water |

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiments of the present invention.

What is claimed is:

1. A surgical cement for orthopedic, dental, and maxillofacial applications, comprising:
   a cementing component selected from the group of a basic calcium phosphate consisting of tetracalcium phosphate, alpha-tricalcium phosphate, decomposed hydroxyapatite, and a combination thereof;
a setting reagent selected from the group of an acidic calcium citrate consisting of monocalcium citrate, dicalcium citrate, and a combination thereof; and
water;
wherein a weight ratio of the cementing component and the setting reagent ranges from about 1:1 to about 8:1.

2. The surgical cement of claim 1, wherein the decomposed hydroxyapatite is partially or fully decomposed hydroxyapatite comprising tetracalcium phosphate and alpha-tricalcium phosphate.

3. The surgical cement of claim 1, having a setting time of about 3 minutes to about 20 minutes.

4. The surgical cement of claim 3, further having the setting time of about 5 minutes to 15 minutes.

5. The surgical cement of claim 1, further comprising a biocompatible filler.

6. The surgical cement of claim 5, wherein the biocompatible filler is up to about 80% by weight based on a total weight of the surgical cement.

7. The surgical cement of claim 5, wherein the biocompatible filler is selected from a group consisting of alpha-tricalcium phosphate, beta-tricalcium phosphate, tetracalcium phosphate, octacalcium phosphate, calcium phosphate apatite, dicalcium phosphate dihydrate, dicalcium phosphate anhydrous, calcium carbonate, coral, calcium sulfate dihydrate, calcium sulfate hemihydrate, calcium sulfate anhydrous, calcium oxide, calcium hydroxide, calcium fluoride, magnesium oxide, magnesium hydroxide, calcium citrate, gelatin, collagen, chitosan, chitin, mineralized collagen, and a combination thereof.

8. The surgical cement of claim 5, wherein the biocompatible filler has a particle size ranging from 5 μm to 2 mm.

9. The surgical cement of claim 1, further comprising a soluble pH adjusting reagent.

10. The surgical cement of claim 9, wherein the soluble pH adjusting reagent is selected from the group consisting of phosphoric acid, citric acid, NaOH, KOH, $NH_4OH$, $Na_3$ Citrate, $K_3$ Citrate, $(NH_4)_3$ Citrate, $Na_3PO_4$, $K_3PO_4$, and a combination thereof.

11. The surgical cement of claim 1, further comprising an antibiotic, a drug, a bone growth factor, or a bone morphogenetic protein.

12. The surgical cement of claim 1, wherein the antibiotic is up to about 20% by weight based on a total weight of the surgical cement.

13. A method of manufacturing surgical cement for orthopedic, dental, and maxillofacial applications, comprising the steps of:
admixing a basic calcium phosphate cementing component and an acidic calcium citrate setting reagent by a weight ratio ranging from about 1:1 to about 8:1;
adding a desired amount of water to obtain a mixture; and
kneading the mixture to obtain a cementitious paste;
wherein the basic calcium phosphate cementing component is selected from the group consisting of tetracalcium phosphate, alpha-tricalcium phosphate, decomposed hydroxyapatite, and a combination thereof; and the acidic calcium citrate setting reagent is selected from the group consisting of monocalcium citrate, dicalcium citrate, and a combination thereof.

14. The method of claim 13, wherein the decomposed hydroxyapatite is decomposed partially or fully to form alpha-tricalcium phosphate and tetracalcium phosphate before the admixing step.

15. The method of claim 13, wherein the cementitious paste has a setting time of about 5 minutes to about 15 minutes.

16. The method of claim 15, wherein the cementitious paste is able to be molded into any desired shape, and is able to stay in water without disintegration before setting.

17. The method of claim 13, further comprising a step of adding a biocompatible filler to mix with the basic calcium phosphate cementing component and the acidic calcium citrate setting reagent before the adding step.

18. The method of claim 17, wherein the biocompatible filler is selected from a group consisting of alpha-tricalcium phosphate, beta-tricalcium phosphate, tetracalcium phosphate, octacalcium phosphate, calcium phosphate apatite, dicalcium phosphate dihydrate, dicalcium phosphate anhydrous, calcium carbonate, coral, calcium sulfate dihydrate, calcium sulfate hemihydrate, calcium sulfate anhydrous, calcium oxide, calcium hydroxide, calcium fluoride, magnesium oxide, magnesium hydroxide, calcium citrate, gelatin, collagen, chitosan, chitin, mineralized collagen, and a combination thereof.

19. The method of claim 18, wherein the biocompatible filler has a particle size ranging from 5 μm to 2 mm.

20. The method of claim 13, further comprising a step of adding a soluble pH adjusting reagent.

21. The method of claim 13, further comprising a step of adding an antibiotic, a drug, a bone growth factor, or a bone morphogenetic protein.

\* \* \* \* \*